(12) United States Patent
Sakai et al.

(10) Patent No.: US 8,663,094 B2
(45) Date of Patent: Mar. 4, 2014

(54) IN-VIVO INFORMATION ACQUIRING SYSTEM

(75) Inventors: Youhei Sakai, Ina (JP); Ken Sato, Nagano (JP)

(73) Assignee: Olympus Corporation, Tokyo (JP)

(*) Notice: Subject to any disclaimer, the term of this patent is extended or adjusted under 35 U.S.C. 154(b) by 825 days.

(21) Appl. No.: 12/748,852

(22) Filed: Mar. 29, 2010

(65) Prior Publication Data
US 2010/0249504 A1   Sep. 30, 2010

(30) Foreign Application Priority Data
Mar. 31, 2009  (JP) ................................ 2009-086698

(51) Int. Cl.
*A61B 1/04*   (2006.01)

(52) U.S. Cl.
USPC ........................... 600/118; 600/103; 600/117

(58) Field of Classification Search
USPC .................... 600/118, 109, 103, 117
See application file for complete search history.

(56) References Cited

U.S. PATENT DOCUMENTS

| | | | |
|---|---|---|---|
| 6,115,647 A * | 9/2000 | Carli et al. | |
| 6,166,518 A * | 12/2000 | Echarri et al. | 320/106 |
| 6,453,198 B1 * | 9/2002 | Torgerson et al. | 607/29 |
| 6,918,872 B2 * | 7/2005 | Yokoi et al. | 600/129 |
| 8,257,248 B2 * | 9/2012 | Yoshizawa et al. | 600/118 |
| 2006/0004255 A1 * | 1/2006 | Iddan et al. | 600/160 |
| 2006/0155174 A1 * | 7/2006 | Glukhovsky et al. | 600/301 |
| 2007/0129602 A1 * | 6/2007 | Bettesh et al. | 600/118 |
| 2008/0009671 A1 * | 1/2008 | Kimoto et al. | 600/109 |
| 2008/0167523 A1 * | 7/2008 | Uchiyama et al. | 600/114 |
| 2009/0018395 A1 * | 1/2009 | Honda | 600/118 |
| 2009/0192353 A1 * | 7/2009 | Segawa | 600/118 |
| 2010/0249508 A1 * | 9/2010 | Sato et al. | 600/117 |
| 2010/0249509 A1 * | 9/2010 | Yoshizawa | 600/118 |
| 2010/0261959 A1 * | 10/2010 | Doi | 600/109 |
| 2010/0261963 A1 * | 10/2010 | Yoshizawa | 600/117 |
| 2012/0232344 A1 * | 9/2012 | Sato et al. | 600/109 |

FOREIGN PATENT DOCUMENTS

| | | |
|---|---|---|
| JP | 2008-012036 | 1/2008 |
| JP | 4139296 | 6/2008 |

OTHER PUBLICATIONS

English abstract of JP 2005-081005.

* cited by examiner

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An in-vivo observation system provided with a capsule endoscope including an in-vivo observation section, a battery, a magnetic field detection section, a power supply switch that controls a power supply and a power supply control section that causes the power supply switch to operate according to an internal signal from the magnetic field detection section, and a magnetic field generating apparatus including a magnetic field generating section, an operation section that outputs an operation signal according to an operation by a user and a masking section that masks an operation signal inputted to the magnetic field generating section for a predetermined period.

6 Claims, 6 Drawing Sheets

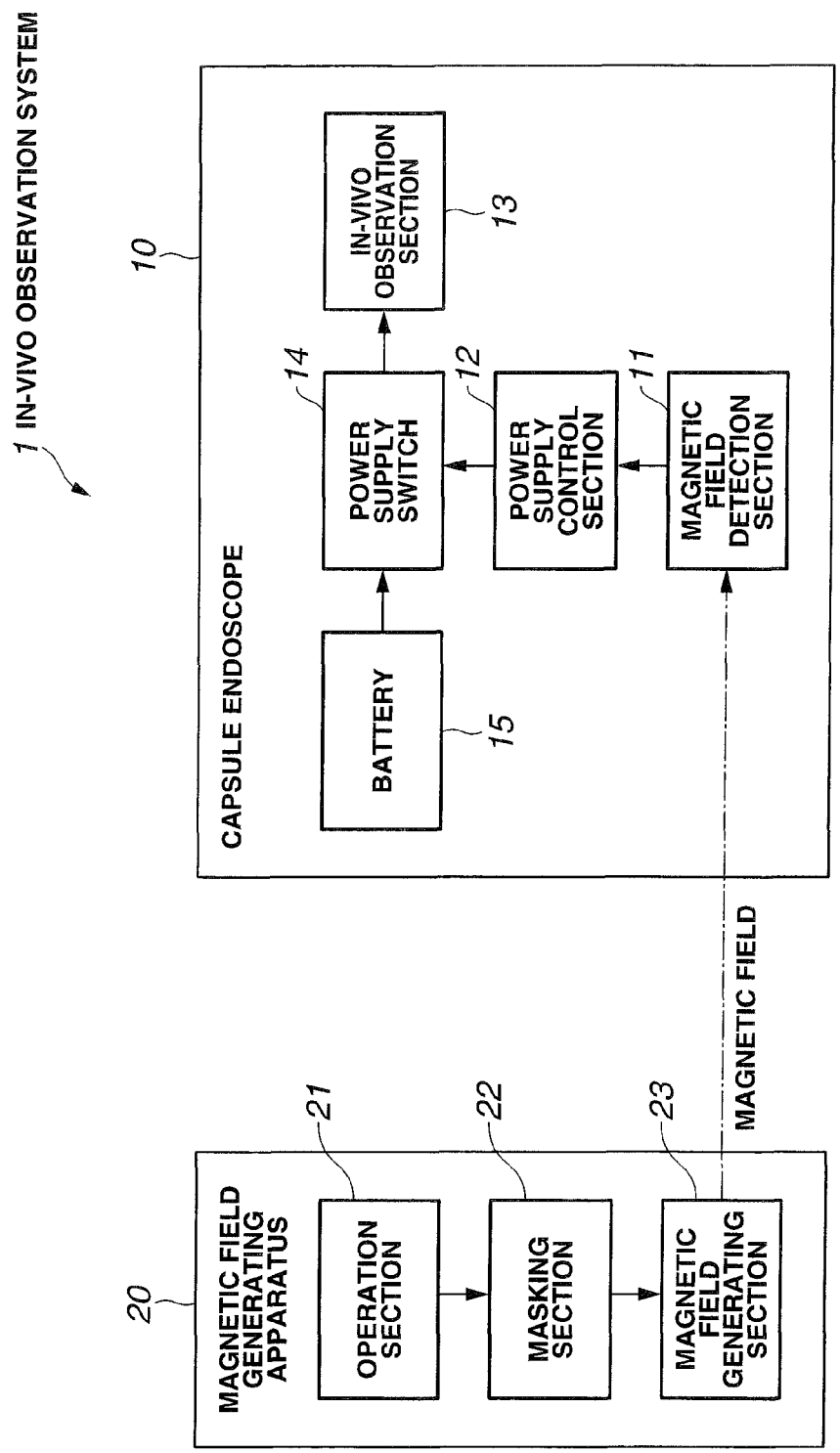

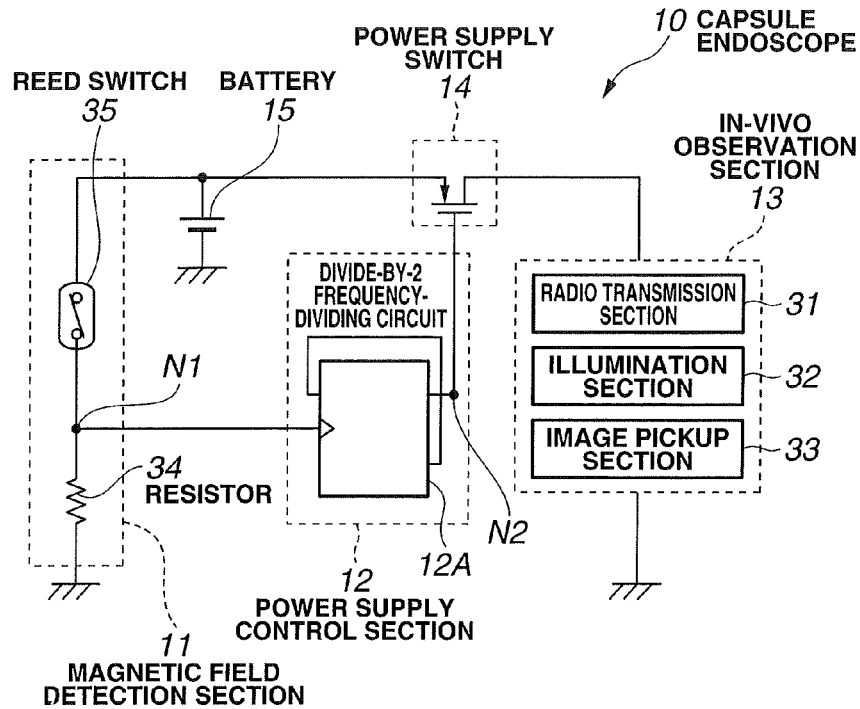
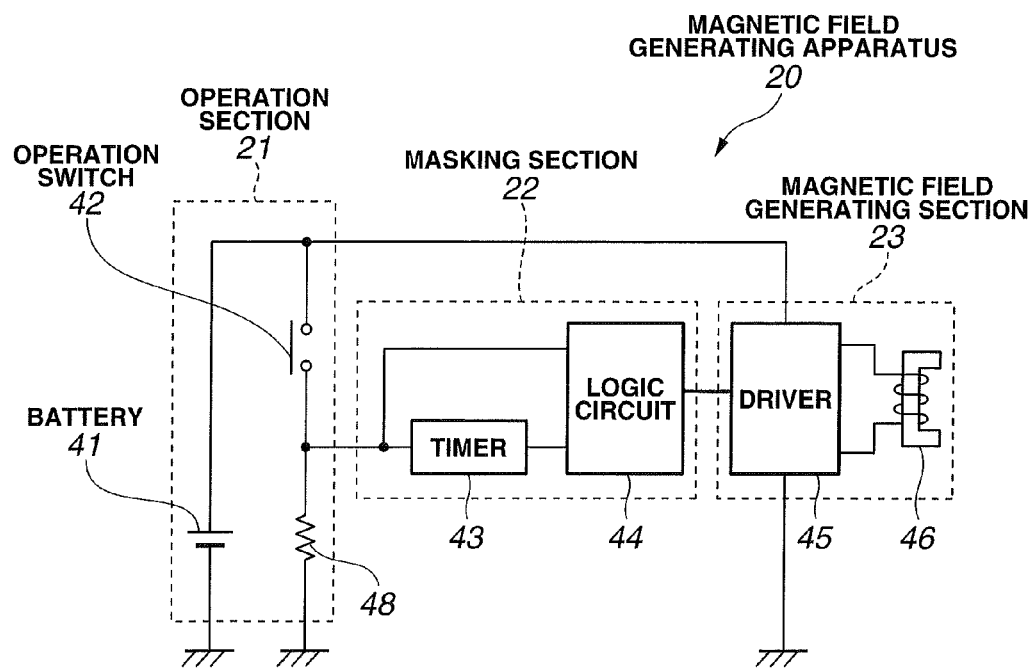

IN-VIVO INFORMATION ACQUIRING SYSTEM

This application claims the benefit of Japanese Application No. 2009-086698 filed in Japan on Mar. 31, 2009, the contents of which are incorporated herein by this reference.

BACKGROUND OF THE INVENTION

1. Field of the Invention

The present invention relates to an in-vivo information acquiring system provided with an in-vivo information acquiring apparatus introduced into an object to be examined and an external signal generating apparatus disposed outside the in-vivo information acquiring apparatus to operate the in-vivo information acquiring apparatus.

2. Description of the Related Art

In recent years, swallow capsule type endoscopes are making their debuts in the field of endoscopes. A capsule endoscope is introduced into a body by being swallowed from an examinee's mouth and moves inside the body cavity, for example, organs such as stomach or small intestine according to peristaltic movement and picks up images one by one until the capsule endoscope is spontaneously discharged.

Image data picked up in the body by the capsule endoscope while the capsule endoscope moves through the body cavity are transmitted one by one to the outside through wireless communication and stored in a memory provided in an outside receiver. After swallowing the capsule endoscope, a patient can freely act by carrying the receiver until the capsule endoscope is discharged.

The capsule endoscope obtains drive power from a battery or the like which is built in a casing, but since the capsule endoscope has a structure with an inner circuit or the like hermetically sealed in the casing, a user cannot perform ON/OFF operation to drive the endoscope by operating a switch or the like disposed on the outer surface of the casing. Thus, a capsule endoscope system is proposed which is provided with a reed switch short-circuited/released by an outside magnetic field in the casing of a capsule endoscope and a permanent magnet in a package in which the capsule endoscope is accommodated and held. The reed switch is structured so as to maintain a released state in an environment in which an outside magnetic field of predetermined intensity or more is given and be short-circuited when the intensity of the outside magnetic field decreases.

Therefore, when the capsule endoscope is accommodated in the package provided with the permanent magnet, the capsule endoscope does not operate before use, but starts to operate when the capsule endoscope is taken out of the package and is not affected by the permanent magnet. This allows the capsule endoscope to prevent battery consumption before the start of use.

Furthermore, a capsule endoscope disclosed by the present applicant in Japanese Patent Publication No. 4139296 turns ON/OFF a power supply from a battery to function executing sections such as an image pickup section through a toggle operation in response to an external signal such as a magnetic field. Thus, the user can perform ON/OFF operation on the capsule endoscope through an external signal even after taking the capsule endoscope out of the package.

Here, the switch may be repeatedly short-circuited/released in a short time due to chattering of the switch operated by the user to generate an external signal, misoperation by the user, or the like. The interval of the toggle operation is then shortened.

However, a measure should be taken for the capsule endoscope to prevent the interval of the toggle operation from becoming short to secure a time necessary to reset an inner circuit.

In order to solve this problem, the present applicant discloses a capsule endoscope 110 shown in FIG. 1 in Japanese Patent Application Laid-Open Publication No. 2008-12036. In addition to a reed switch 135 that turns ON/OFF according to intensity of a DC magnetic field, the capsule endoscope 110 includes a mask signal generation circuit 123 for masking a switch signal Vin from the reed switch 135 for a predetermined period.

When the reed switch 135 is OFF, the switch signal Vin is at a power supply voltage level, and therefore a P-MOS transistor 144 turns OFF and an N-MOS transistor 145 turns ON. A charge stored in a capacitor 147 is then gradually discharged according to a time constant determined by a resistor 146 and the capacitor 147 and a signal Vmask is outputted. On the other hand, when the reed switch 135 is ON, the signal Vin at a ground voltage level is outputted, and therefore the P-MOS transistor 144 turns ON and the N-MOS transistor 145 turns OFF. The capacitor 147 is then charged and the signal Vmask is outputted as a power supply voltage level.

Here, an inverter 141 outputs a signal Vout1 which changes from a ground voltage level to a power supply voltage level when the value of the signal Vmask falls to or below a predetermined value Vth. When charging/discharging of the capacitor 147 is repeated and the signal Vmask does not fall to or below Vth, a mask period is formed during which even if the signal Vin changes, the change is not transmitted.

Here, the signal Vout1 is inputted to an inverter 142 and the inverter 142 outputs a signal Vout2 which is obtained by inverting the inputted signal Vout1 to a divide-by-2 frequency-dividing circuit 143. The divide-by-2 frequency-dividing circuit 143 divides the inputted signal Vout2 by 2 as an ON/OFF control signal Vout and applies Vout to a gate of a power supply switch 114. Since the power supply switch 114 is a P-MOS transistor, the power supply switch 114 turns ON when Vout is at a ground voltage level.

Since the capsule endoscope 110 has the mask signal generation circuit 123 using a charging/discharging circuit, even if the intensity of the magnetic field from the outside magnetic field generating section is unstable, the interval of toggle operation is never shortened.

SUMMARY OF THE INVENTION

An in-vivo information acquiring system according to the present invention includes an in-vivo information acquiring apparatus introduced into an object to be examined, including an in-vivo information acquiring section that acquires information inside the object to be examined, a power supply source that supplies power to be used to drive the in-vivo information acquiring section, an external signal detection section that detects an external signal and outputs an internal signal according to the detected external signal, a power switch that controls a power supply from the power supply source to the in-vivo information acquiring section and a power supply control section that causes the power switch to operate according to the internal signal inputted from the external signal detection section, and an external signal generating apparatus disposed outside the in-vivo information acquiring apparatus, including an external signal generating section that generates the external signal, an operation section that outputs an operation signal instructing the external signal generating section to generate the external signal according to an operation and a masking section that masks the operation signal from the operation section to the external signal generating section for a predetermined period.

BRIEF DESCRIPTION OF THE DRAWINGS

FIG. 2 is a block diagram illustrating a schematic configuration of an in-vivo observation system according to a first embodiment;

FIG. 3 is a block diagram illustrating a schematic configuration of a capsule endoscope of the first embodiment;

FIG. 4 is a block diagram illustrating a schematic configuration of a magnetic field generating apparatus of the first embodiment;

DETAILED DESCRIPTION OF THE PREFERRED EMBODIMENT(S)

First Embodiment

Figure 1:
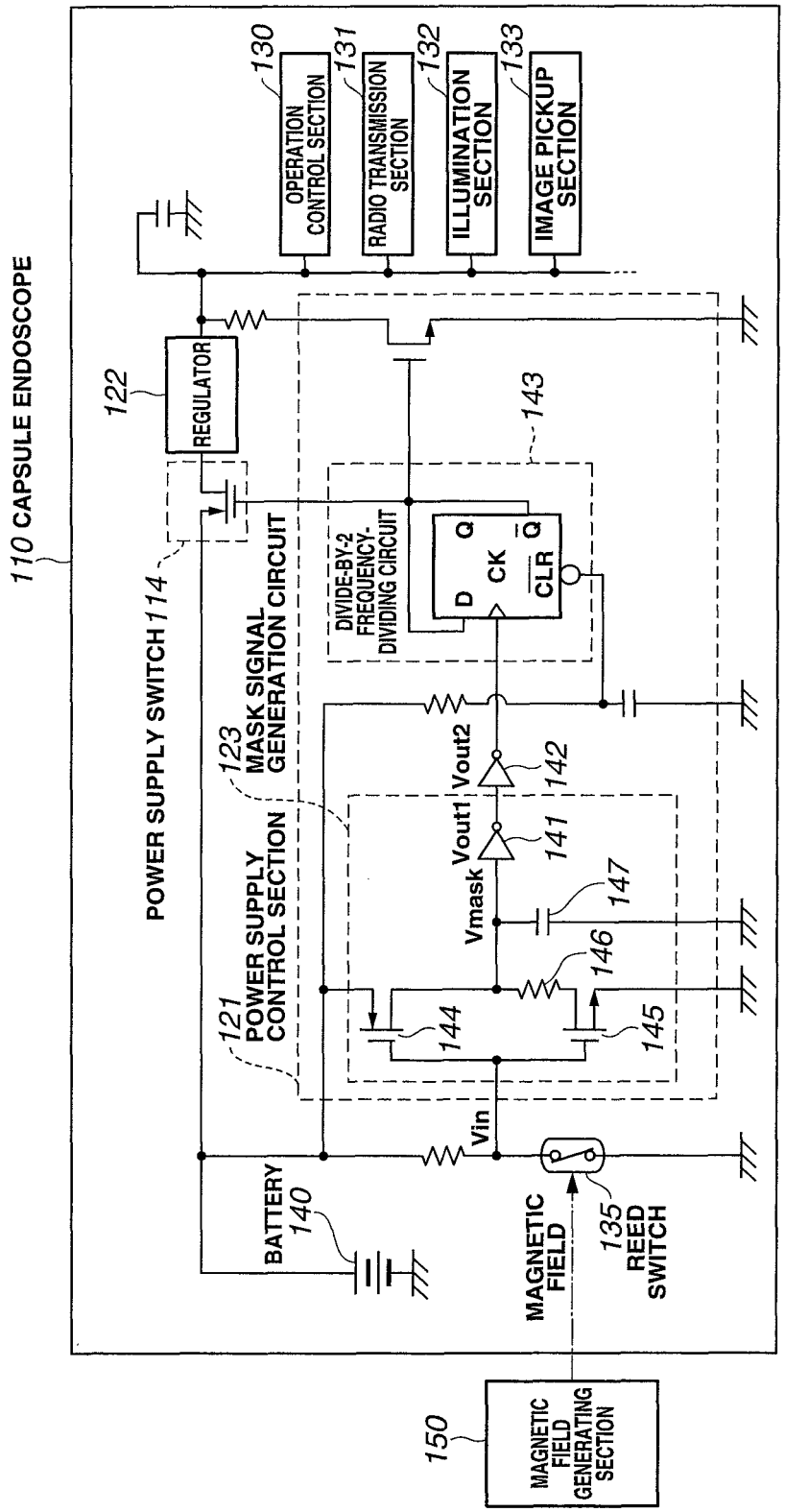
FIG. 1 is a block diagram illustrating a configuration of a publicly known capsule endoscope.

An in-vivo observation system 1, which is an in-vivo information acquiring system according to a first embodiment of the present invention, will be described below using FIG. 2 to FIG. 5. As shown in FIG. 2, the in-vivo observation system 1 of the present embodiment is provided with a capsule endoscope 10, which is for acquiring in-vivo information and introduced into an object to be examined and a magnetic field generating apparatus 20 disposed outside the capsule endoscope 10, which is an external signal generating apparatus, that generates a magnetic field signal (hereinafter also simply referred to as "magnetic field") for operating the capsule endoscope 10. That is, an in-vivo observation section 13 of the capsule endoscope 10 is operated to turn ON/OFF by a magnetic field signal from the magnetic field generating apparatus 20.

The capsule endoscope 10 has the in-vivo observation section 13, a battery 15, a magnetic field detection section 11, a power supply switch 14 and a power supply control section 12. The in-vivo observation section 13 is an in-vivo information acquiring section that acquires an image in the body of the object to be examined. The battery 15 is a power supply source that supplies drive power to the in-vivo observation section 13. The magnetic field detection section 11 is an external signal detection section that detects a DC magnetic field signal, which is an external signal inputted from the magnetic field generating apparatus 20, and outputs an internal signal according to the detected magnetic field. The power supply switch 14 is a power switch that controls a power supply from the battery 15 to the in-vivo observation section 13. The power supply control section 12 causes the power supply switch 14 to perform a toggle operation according to the internal signal inputted from the magnetic field detection section 11.

On the other hand, the magnetic field generating apparatus 20 includes a magnetic field generating section 23 that generates a DC magnetic field, an operation section 21 that outputs an operation signal to instruct the magnetic field generating section 23 to generate a DC magnetic field in response to an operation and a masking section 22 for masking the operation signal from the operation section 21 to be inputted to the magnetic field generating section 23 for a predetermined period.

Next, the structure of the capsule endoscope 10 will be further described using FIG. 3. The capsule endoscope 10 has the in-vivo observation section 13, which is a main function, and the in-vivo observation section 13 has an illumination section 32, an image pickup section 33 and a radio transmission section 31. The illumination section 32 has an LED (not shown) to irradiate an image pickup region with light when photographing the inside of the body of the object to be examined and an LED drive circuit (not shown) that controls a drive state of the LED. The image pickup section 33 has a CCD (not shown) that picks up an image of the region irradiated by the LED and a signal processing circuit (not shown) that processes the image signal outputted from the CCD into image data in a desired format. The radio transmission section 31 has an RF transmission unit (not shown) that modulates the image data picked up and processed by the CCD and generates an RF signal and a transmission antenna section (not shown) that transmits the RF signal outputted from the RF transmission unit. Although the LED has been illustrated as illumination means, the illumination means is not limited thereto as long as such means can irradiate the image pickup region. Furthermore, although the CCD has been illustrated as the image pickup section, the image pickup section is not limited thereto as long as such image pickup section can pick up images and, for example, a CMOS sensor or the like may also be used.

The capsule endoscope 10 of the in-vivo observation system 1 of the present embodiment has the magnetic field detection section 11 that detects a DC magnetic field, which is an external signal for instructing turning ON/OFF of a power supply to the in-vivo observation section 13. The magnetic field detection section 11 has a reed switch 35 and a resistor 34. The reed switch 35 includes two ferromagnetic reeds placed opposed to each other with a gap in-between at one end and sealed in a glass tube. When a magnetic field equal to or above a predetermined threshold is applied from outside to the reed switch 35, an N pole or an S pole is induced to each reed and the two reeds are short-circuited by this magnetic attractive force. When the magnetic field falls below the predetermined threshold, the reed switch 35 goes into a released state by elasticity of the reeds.

That is, when the magnetic field detection section 11 detects, no magnetic field, the reed switch 35 is in a released state, and therefore the magnetic field detection section 11 outputs a signal at a ground voltage level to a node N1. When the magnetic field detection section 11 detects a magnetic field, the reed switch 35 is in a short-circuited state, and therefore the magnetic field detection section 11 outputs a signal at a power supply voltage level from the battery 15 to the node N1. Hereinafter, a signal outputted to the node N1 will be referred to as an "internal signal." That is, the internal signal is a pulse signal at a power supply voltage level/ground voltage level corresponding to detection/non-detection of a magnetic field.

A divide-by-2 frequency-dividing circuit 12A, which is the power supply control section 12, has a D-type flip flop circuit and outputs a signal obtained by dividing an internal signal by 2 to the power supply switch 14. As a result, one operation of the magnetic field detection section 11 causes the power supply switch 14 to perform a toggle operation of switching between ON and OFF states. That is, one operation of the magnetic field detection section 11 detecting a magnetic field causes the power supply switch 14 to turn from an OFF state to an ON state or from an ON state to an OFF state. When the short-circuiting/releasing operation of the reed switch 35 is not performed, the power supply switch 14 maintains an ON or an OFF state. That is, the state of the power supply switch 14 is maintained although the magnetic field detection section 11 does not continue to apply a magnetic field to the reed switch 35. That is, the power supply control section 12 functions as state maintaining means of the power supply switch 14. The D-type flip flop circuit of the power supply control section 12 may be any other circuit as long as such a circuit can divide the input signal by 2, and may be a T-type flip flop circuit or the like.

Here, the power supply switch 14 is a P-MOS transistor, a source of which is connected to the battery 15, a drain of which is connected to the in-vivo observation section 13, which is the main function section of the capsule endoscope 10 and a gate of which is connected to the divide-by-2 frequency-dividing circuit 12A. As has already been described, when the output signal of the divide-by-2 frequency-dividing circuit 12A is at a power supply voltage level, the power supply switch 14 is OFF and power is not supplied to the in-vivo observation section 13. Conversely, when the output signal of the divide-by-2 frequency-dividing circuit 12A is at a ground voltage level, the power supply switch 14 is ON and power is supplied to the in-vivo observation section 13. That is, when the magnetic field is applied or stopped by one pulse, the in-vivo observation section 13 of the capsule endoscope 10 performs a toggle operation between an ON state and an OFF state per one pulse.

Next, the magnetic field generating apparatus 20 of the in-vivo observation system 1 of the present embodiment will be described using FIG. 4. As has already been described, the magnetic field generating apparatus 20 generates a DC magnetic field, which is an external signal for causing the capsule endoscope 10 to perform a start/stop (ON/OFF) operation of the in-vivo observation section 13.

An operation switch 42 of the operation section 21 is a switch operated by a user and is, for example, a push button switch. The operation section 21 outputs to the masking section 22 operation signals of two levels: power supply voltage level and ground voltage level corresponding to short-circuiting/releasing of the operation switch 42. That is, the operation signal is a pulse signal of a predetermined pulse width at a power supply voltage level superimposed on a signal at a ground voltage level. Therefore, the pulse width of the operation signal corresponds to the time of the power supply voltage level during which the operation switch 42 is in a short-circuited state. FIG. 4 shows a battery 41 as a component of the operation section 21, but the battery 41 is also a component of the magnetic field generating section 23 or the like.

The masking section 22 has a timer 43 and a logic circuit 44. The timer 43 measures time and outputs a time-lapse signal to the logic circuit 44 when a predetermined time elapses. The logic circuit 44, which has received the time-lapse signal from the timer 43, outputs an operation signal to a driver 45.

As described above, the timer 43 may be, for example, a counter circuit having a counter and an oscillator, a time constant circuit with CR, or the like as long as such a circuit is a pulse width extension section that extends the pulse width (short circuit time of the operation switch 42) for a predetermined period (T1) of an operation signal. For example, a charging/discharging circuit using a P-MOS transistor, an N-MOS transistor, a resistor and a capacitor disclosed by the present applicant in Japanese Patent Application Laid-Open Publication No. 2008-12036 may also be used as the masking section 22.

In response to the signal inputted from the masking section 22, the driver 45 controls whether or not to apply the DC current from the battery 15 to an electromagnet 46. The electromagnet 46 generates a DC magnetic field by application of the DC current from the driver 45.

Figure 5:
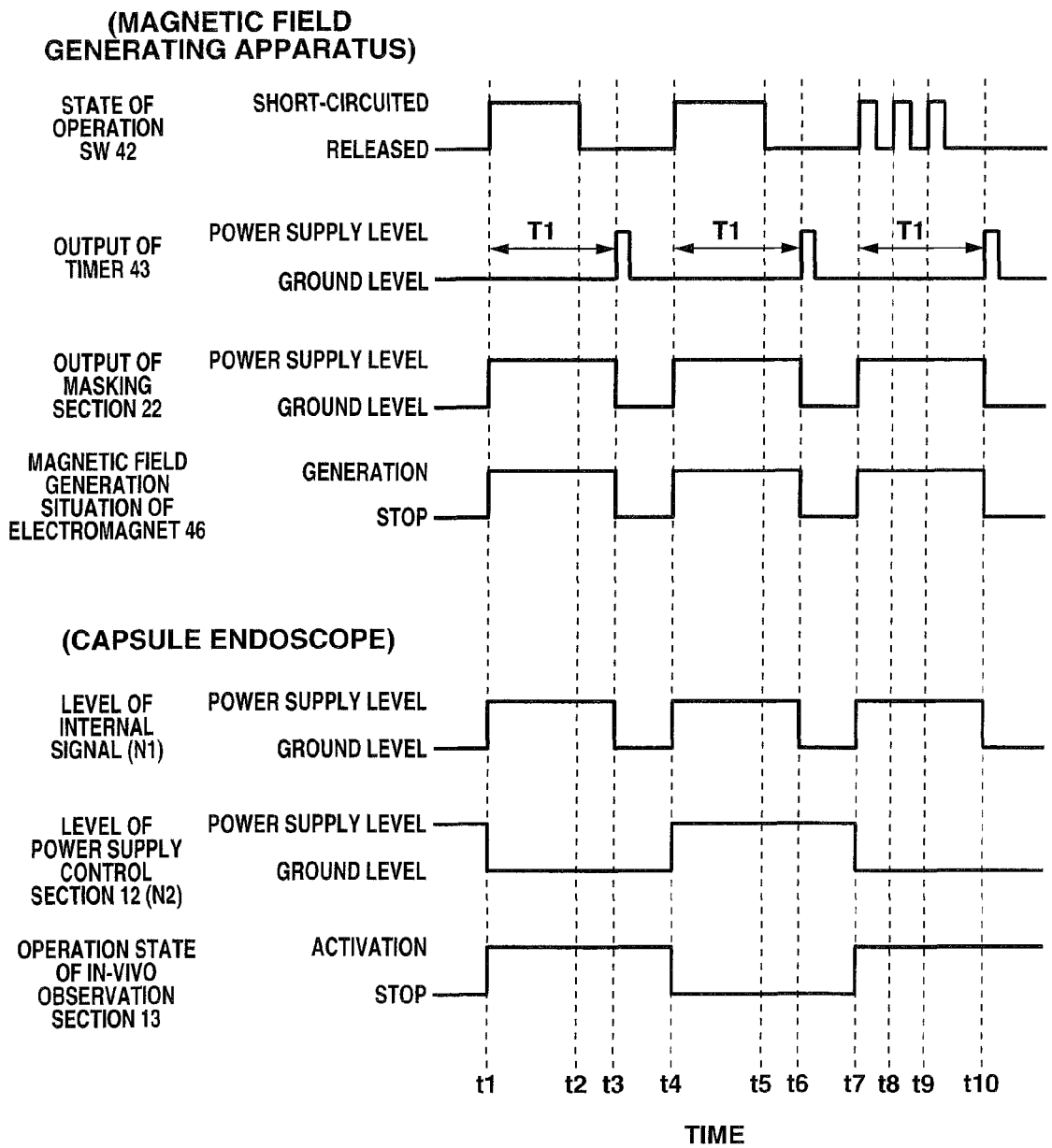
FIG. 5 is a time chart illustrating operations of the in-vivo observation system according to the first embodiment.

Next, operations of the in-vivo observation system 1 according to the present embodiment will be described using a time chart in FIG. 5.

(Time t1) When the operation switch (SW) 42 is pressed by the user and the operation switch 42 goes into a short-circuited state, the signal outputted from the masking section 22 becomes a power supply voltage level, the driver 45 applies a predetermined DC current to the electromagnet 46 and the electromagnet 46 generates a DC magnetic field, which is an external signal.

The reed switch 35 of the capsule endoscope 10 is then short-circuited by the DC magnetic field, which is the external signal from the electromagnet 46. This causes the internal signal (node N1) to become the power supply voltage level. Furthermore, since the output signal (node N2) of the divide-by-2 frequency-dividing circuit 12A becomes the ground voltage level, the power supply switch 14 turns to an ON state and the in-vivo observation section 13 of the capsule endoscope 10 starts to operate.

The power supply voltage level of the capsule endoscope 10 is the voltage of the battery 15 and the power supply voltage level of the magnetic field generating apparatus is the voltage of the battery 41, but both voltages may be different or the same.

On the other hand, the timer 43 starts to measure time simultaneously with the short-circuiting of the operation switch 42.

(Time t2) When the user stops pressing the operation switch 42, the operation switch 42 goes into a released state and the operation signal becomes the ground voltage level. However, since time t2 is before time t3 at which the time preset by the timer 43 (predetermined period: T1) elapses, the driver 45 does not receive any operation signal. That is, the operation signal from the operation switch 42 is masked by the masking section 22 for the predetermined period T1 and is not transmitted to the driver 45. Therefore, the DC magnetic field continues to be generated from the electromagnet 46.

(Time t3) When a preset time elapses (period T1), the timer 43 sends a time-lapse signal to the logic circuit 44. The logic circuit 44 which has received the time-lapse signal from the timer 43 outputs the operation signal from the masking section 22. The driver 45 which has received the signal at the ground voltage level from the masking section 22 stops applying a current to the electromagnet 46, and therefore the generation of the DC magnetic field from the electromagnet 46 stops.

When the generation of the DC magnetic field from the electromagnet 46 stops, the reed switch 35 of the capsule endoscope 10 goes into a released open state. Therefore, the magnetic field detection section 11 outputs a signal at the ground voltage level as an internal signal. However, the power supply switch 14 of the capsule endoscope 10 remains ON due to the action of the divide-by-2 frequency-dividing circuit 12A and the in-vivo observation section 13 continues operating.

(Time t4 to t6) When the operation switch 42 is short-circuited again, each component repeats the aforementioned operation and since the power supply switch 14 turns OFF, the in-vivo observation section 13 of the capsule endoscope 10 which is activating the in-vivo observation section 13 transitions to a stopped state. That is, every time the user presses the operation switch 42, the in-vivo observation section 13 toggles between an activated state and a stopped state.

(Time t7 to t9) This indicates a state in which the short-circuiting/releasing of the operation switch 42 is repeated within a short time due to misoperation or the like during a period (T1) which the timer 43 is measuring. At time t7, each component repeats the aforementioned operation and the in-vivo observation section 13 transitions from a stopped state to an activated state. After that, the operation switch 42 repeats short-circuiting/releasing many times for a short time, but since the operation signal from the operation switch 42 is masked by the masking section 22, the output of the masking section 22 is maintained for a predetermined period (T1) and the generation of the magnetic field from the electromagnet 46 never stops.

As described above, in the in-vivo observation system according to the present embodiment, even if the operation switch 42 of the magnetic field generating apparatus 20 is short-circuited/released many times within a short time due to chattering or misoperation or the like, the generation of the magnetic field from the magnetic field generating apparatus 20 is maintained for the predetermined period (T1). Therefore, the in-vivo observation section 13 in the capsule endoscope 10 can secure a necessary reset period and perform stable activation/stop.

Since the magnetic field generating apparatus 20 has the masking section 22 to secure the reset period and there is no possibility that any unstable magnetic field may be generated, the masking section need not be provided in the capsule endoscope 10. Thus, the capsule endoscope 10 can be downsized. Moreover, since the capsule endoscope 10 has no masking section, power consumption is low and a necessary observation time can be secured.

That is, it is possible to provide the in-vivo observation system 1 including the small and low power consumption capsule endoscope 10 and the magnetic field generating apparatus 20 that outputs a stable external signal for a power supply operation of the capsule endoscope 10.

Second Embodiment

An in-vivo observation system 1A, which is an in-vivo information acquiring system according to a second embodiment of the present invention will be described below using FIG. 6 to FIG. 8. Since the in-vivo observation system 1A of the present embodiment is similar to the in-vivo observation system 1 according to the first embodiment, components having the same functions will be assigned the same reference numerals and descriptions thereof will be omitted.

While the in-vivo observation system 1 of the first embodiment uses a DC magnetic field as an external signal, the in-vivo observation system 1A of the present embodiment uses an AC magnetic field as an external signal. That is, the in-vivo observation system 1A has an AC magnetic field generating apparatus 20A that generates an AC magnetic field and a capsule endoscope 10A having an AC magnetic field detection section 11A.

Figure 6:
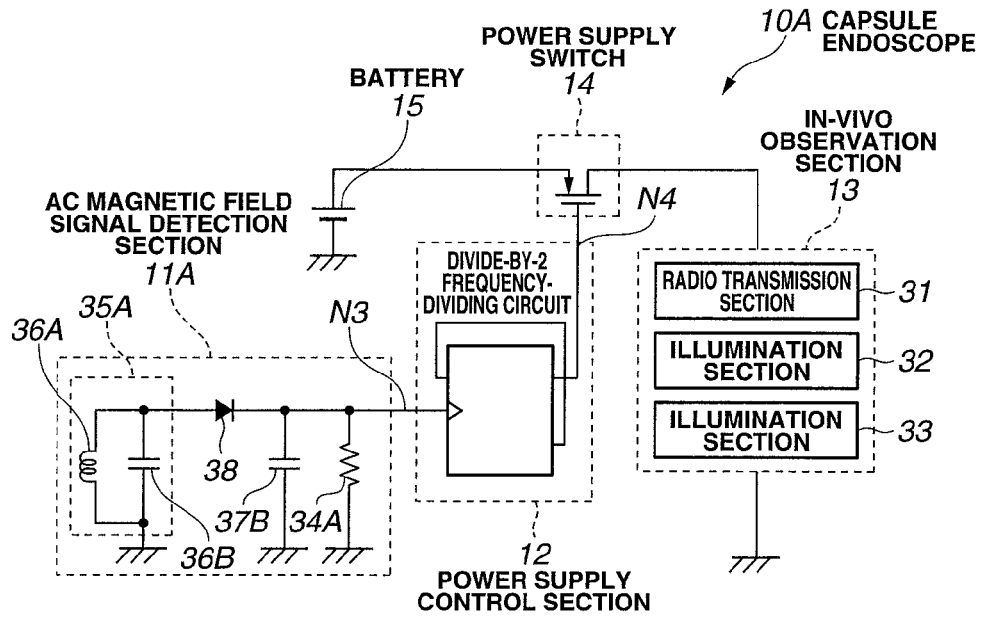
FIG. 6 is a block diagram illustrating a schematic configuration of a capsule endoscope according to a second embodiment.

As shown in FIG. 6, the AC magnetic field detection section 11A, which is an external signal detection section of the capsule endoscope 10A of the in-vivo observation system 1A according to the present embodiment, has a receiving antenna 35A that detects an AC magnetic field from the AC magnetic field generating apparatus 20A, a diode 38 that rectifies an AC signal received through the receiving antenna 35A, a smoothing capacitor 37B that smoothes the AC signal and a resistor 34A that discharges the electric charge charged in the smoothing capacitor 37B. The receiving antenna 35A is a resonance circuit that has a secondary side coil 36A and a secondary side capacitor 36B and is adjusted so as to resonate with the frequency of the AC magnetic field from outside. That is, since the capsule endoscope 10A electromagnetically converts the received AC magnetic field and obtains a DC voltage signal, there is no need for a power supply for the AC magnetic field detection section 11A to detect the magnetic field.

Figure 7:
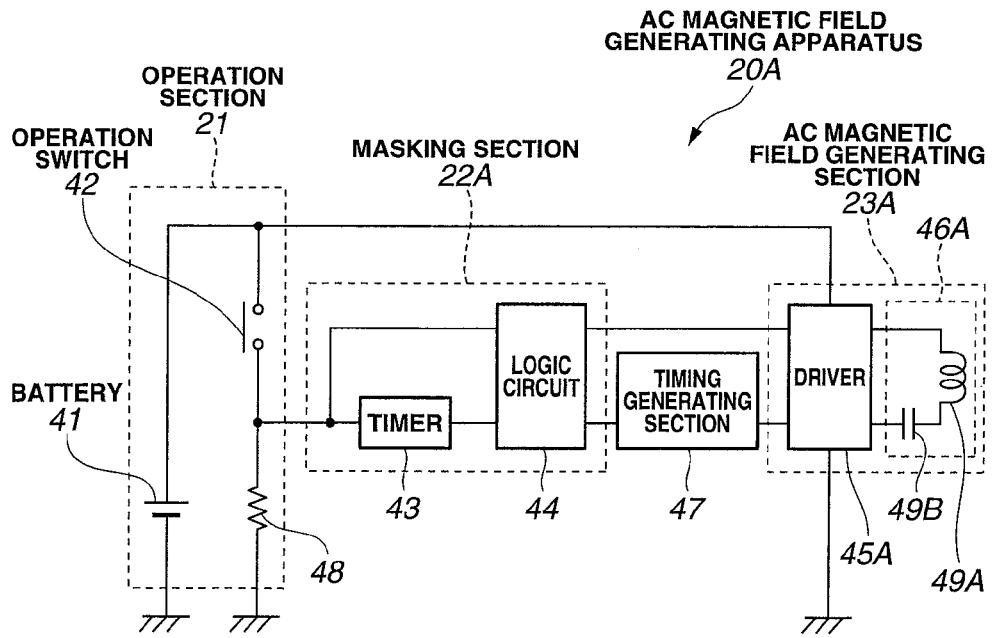
FIG. 7 is a block diagram illustrating a schematic configuration of a magnetic field generating apparatus according to the second embodiment.
Figure 8:
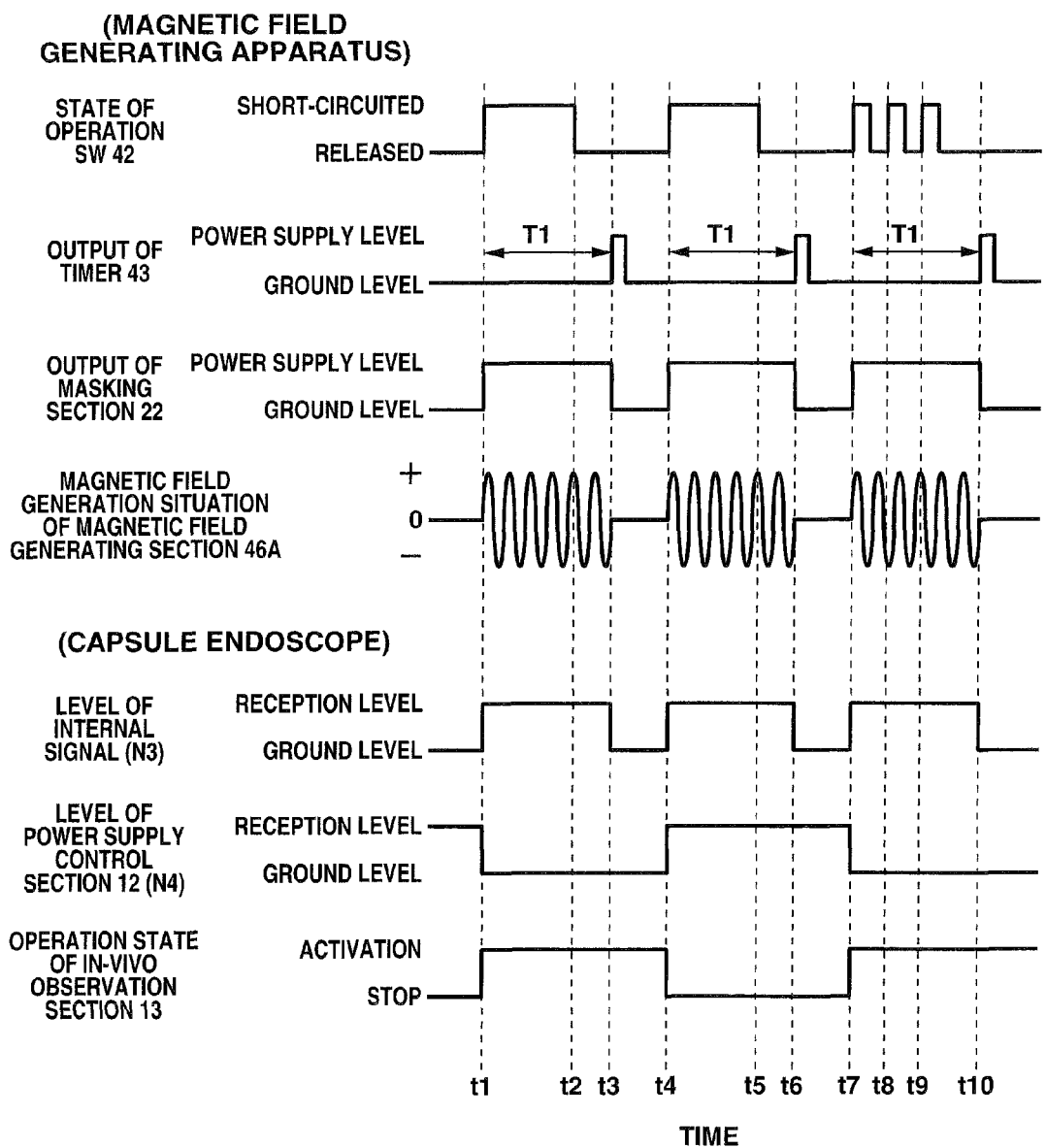
FIG. 8 is a time chart illustrating operations of an in-vivo observation system according to the second embodiment.

As shown in FIG. 7, the AC magnetic field generating apparatus 20A of the in-vivo observation system 1A of the present embodiment has a timing generating section 47 and an AC magnetic field generating section 23A. A transmission antenna 46A of the AC magnetic field generating section 23A constitutes a resonance circuit including a primary side coil 49A and a primary side capacitor 49B. The timing generating section 47 performs processing of setting a signal from an oscillator (not shown) to a desired frequency or the like and transmits the signal of the frequency to a driver 45A. The driver 45A drives the transmission antenna 46A using the inputted signal and the transmission antenna 46A generates an AC magnetic field, which is an external signal of a predetermined frequency corresponding thereto.

Next, operations of the in-vivo observation system 1A according to the present embodiment will be described using the time chart in FIG. 8.

When the operation switch 42 is short-circuited at time t1, the output of a masking section 22A to which an operation signal is inputted becomes a power supply voltage level and an AC magnetic field is generated from the transmission antenna 46A. As has already been described, the frequency of the AC magnetic field generated by the transmission antenna 46A is a frequency adjusted by the timing generating section 47.

The capsule endoscope 10A detects the AC magnetic field, which is an external signal, through the AC magnetic field detection section 11A, which is an external signal detection section. To be more specific, the AC magnetic field generates an AC current in the receiving antenna 35A by means of an electromagnetic induction effect. The detected, that is, received AC magnetic field is rectified by the diode 38, smoothed by the smoothing capacitor 37B and transmitted to the divide-by-2 frequency-dividing circuit 12A as an internal signal of the received voltage level.

That is, when the AC magnetic field detection section 11A detects (receives) the AC magnetic field, the detected signal (node N3), which is an internal signal, becomes a received voltage level. When the received voltage level exceeds a threshold of the divide-by-2 frequency-dividing circuit, the output (node N4) of the divide-by-2 frequency-dividing circuit 12A becomes a ground voltage level, the power supply switch 14 turns to an ON state and the in-vivo observation section 13 of the capsule endoscope 10A starts to operate.

On the other hand, the timer 43 starts to measure time simultaneously with the short-circuiting of the operation switch 42. When a preset time (T1) elapses, the timer 43 sends a time-lapse signal to the logic circuit 44.

Conversely, even if the operation switch 42 is released before the time (T1) preset by the timer 43 elapses and a new operation signal at a ground voltage level is outputted, the driver 45 does not receive any new operation signal. This is because the operation signal from the operation switch 42 is masked by the masking section 22A. For this reason, even if the operation switch 42 is in a released state at time t2, the generation of the AC magnetic field does not stop.

Upon receiving the time-lapse signal from the timer 43, the logic circuit 44 of the masking section 22A outputs an operation signal. The driver 45A, which has received the signal at the ground voltage level from the masking section 22A, stops driving the transmission antenna 46A, that is, stops generating the AC magnetic field.

In this case, although the AC magnetic field detection section 11A of the capsule endoscope 10A outputs an internal signal at the ground voltage level, the operation of the in-vivo observation section 13 is continued by the action of the divide-by-2 frequency-dividing circuit 12. When the operation switch 42 is short-circuited again at time t4, each component repeats the aforementioned operation and the in-vivo observation section 13, which is active, transitions to a stopped state.

That is every time the operation switch 42 is pressed, the in-vivo observation section 13 of the capsule endoscope 10A toggles between an activated state and a stopped state.

Next, operations from time t7 onward will be described.

The period from time t7 onward shows that short-circuiting/releasing of the operation switch 42 is repeated many times for a short time due to misoperation or the like during time (T1) which the timer 43 is measuring.

At time t7, each component repeats the aforementioned operation, the in-vivo observation section 13 of the capsule endoscope 10A transitions from a stopped state to an activated state. After that, although the operation switch 42 repeats short-circuiting/releasing in a short time, since the operation signal from the operation switch 42 is masked by the masking section 22A and maintained for a predetermined period, the generation of the AC magnetic field from the transmission antenna 46A does not stop.

As described so far, the in-vivo observation system 1A of the present embodiment has effects similar to those of the in-vivo observation system 1 of the first embodiment. Furthermore, since the in-vivo observation system 1A uses the AC magnetic field as an external signal, it is possible to downsize the capsule endoscope 10A and save its power more than the in-vivo observation system 1 including the capsule endoscope 10 that detects the DC magnetic field using the reed switch 35. That is, the receiving antenna 35A that detects an AC magnetic field has higher sensitivity than the reed switch 35, that is, can detect a feeble magnetic field. Furthermore, the AC magnetic field detection section 11A does not require any power supply to detect the magnetic field.

Although a case has been described above where a DC magnetic field or an AC magnetic field is used as an external signal, the external signal is not limited thereto, but any one or a combination of two or more of an optical signal, a sound signal and a radio signal may be used.

Furthermore, although a case with the capsule endoscope has been described above as an example, the in-vivo information acquiring system of the present invention is also applicable to various types of capsule in-vivo information acquiring apparatus such as a capsule type medical apparatus for collecting digestive juices or swallow capsule type pH sensor.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An in-vivo information acquiring system comprising:
    an in-vivo information acquiring apparatus introduced into an object to be examined, comprising:
        an in-vivo information acquiring section that acquires information inside the object to be examined;
        a power supply source that supplies power to be used to drive the in-vivo information acquiring section;
        an external signal detection section that detects an external signal and outputs an internal signal according to the detected external signal;
        a power switch that controls a power supply from the power supply source to the in-vivo information acquiring section; and
        a power supply control section that causes the power switch to perform a toggle operation according to the internal signal inputted from the external signal detection section, and
    an external signal generating apparatus disposed outside the in-vivo information acquiring apparatus, comprising:
        an external signal generating section that generates the external signal;
        an operation section that is an operation switch which outputs an operation signal instructing the external signal generating section to generate the external signal according to an operation, the operation switch outputting the operation signal when a pressing operation of the operation switch is performed, and stopping output of the operation signal when the pressing operation is released, to thereby output the operation signal in pulses; and
        a masking section that is a pulse width extension section which extends a pulse width of the operation signal from the operation section to the external signal generating section for a predetermined period.

2. The in-vivo information acquiring system according to claim 1, wherein the pulse width extension section is a timer.

3. The in-vivo information acquiring system according to claim 1, wherein the pulse width extension section is a charging/discharging circuit.

4. The in-vivo information acquiring system according to claim 1, wherein the external signal is any one or a combination of two or more of a DC magnetic field signal, an AC magnetic field signal, an optical signal, a sound signal and a radio signal.

5. The in-vivo information acquiring system according to claim 4, wherein the in-vivo information acquiring apparatus is a capsule endoscope.

6. A capsule endoscope system comprising:
    a capsule endoscope to be introduced into an object to be examined, comprising:
        an in-vivo observation section that acquires an image inside the object to be examined;
        a battery that supplies power used to drive the in-vivo observation section;
        a magnetic field detection section that detects a magnetic field signal and outputs an internal signal according to the detected magnetic field signal;
        a power supply switch that controls a power supply from the battery to the in-vivo observation section; and
        a power supply control section that causes the power supply switch to perform a toggle operation according to the internal signal inputted from the magnetic field detection section, and
    a magnetic field generating apparatus disposed outside the capsule endoscope, comprising:
        a magnetic field generating section that generates the magnetic field signal;
        an operation switch that outputs an operation signal when a pressing operation for outputting the operation signal instructing the magnetic field generating section to generate the magnetic field signal is performed according to an operation by a user, and stops output of the operation signal when the pressing operation is released, to thereby output the operation signal in pulses; and a timer that extends a pulse width of the operation signal to the magnetic field generating section from the operation switch for a predetermined period.

* * * * *